US00PP25891P3

(12) United States Plant Patent
Stoppel

(10) Patent No.: US PP25,891 P3
(45) Date of Patent: Sep. 15, 2015

(54) CHERRY ROOTSTOCK PLANT NAMED 'STO1'

(50) Latin Name: ***Prunus*×*gondouinii* (Poit. & Turpin) Rehder (*P. avium* (L.) L.×*P. cerasus* L.)**
Varietal Denomination: STO1

(71) Applicant: Peter Stoppel Obstbau, Kressbronn (DE)

(72) Inventor: Peter Stoppel, Kressbronn (DE)

( * ) Notice: Subject to any disclaimer, the term of this patent is extended or adjusted under 35 U.S.C. 154(b) by 99 days.

(21) Appl. No.: 13/987,744

(22) Filed: Aug. 27, 2013

(65) Prior Publication Data

US 2015/0067934 P1 Mar. 5, 2015

(51) Int. Cl.
*A01H 5/06* (2006.01)

(52) U.S. Cl.
USPC ..... Plt./183

(58) Field of Classification Search
USPC ..... Plt./183
See application file for complete search history.

(56) References Cited

PUBLICATIONS

UPOV hit on 'STO1', recorded as QZ PBR 20120021, published Apr. 15, 2012, https://www3.wipo.int/pluto/user/en/index.jsp.*
Plant Breeders' Rights Application filed in Turkey on Mar. 23, 2015.
Plant Breeders' Rights Application filed in Europe on Dec. 29, 2011.
Plant Breeders' Rights Application filed in Canada on Apr. 24, 2015.

* cited by examiner

*Primary Examiner* — Anne Grunberg
(74) *Attorney, Agent, or Firm* — Myers Bigel Sibley & Sajovec, PA

(57) ABSTRACT

A new and distinct cultivar of *Prunus* plant named 'STO1,' characterized by its upright plant habit and slow growth; good adaptation at hot and dry conditions; and as a rootstock the slow vegetative growth imparts uniformity, higher yield and better fertility to the grafted variety as compared to a standard rootstock such as Gisela 5, F12/1 and Mazzard.

3 Drawing Sheets

Latin name of the genus and species: The Latin name of the genus and species of the plant variety disclosed herein is *Prunus*×*gondouinii* (Poit. & Turpin) Rehder (*P. avium* (L.) L.×*P. cerasus* L.).

Variety denomination: The inventive cultivar of *Prunus*×*gondouinii* (Poit. & Turpin) Rehder (*P. avium* (L.) L.×*P. cerasus* L.) disclosed herein has been given the varietal denomination 'STO1.'

BACKGROUND OF THE INVENTION

The present invention relates to a new and distinct cultivar of *Prunus* plant, typically used as a cherry tree rootstock, botanically known as *Prunus*×*gondouinii* (Poit. & Turpin) Rehder (*P. avium* (L.) L.×*P. cerasus* L.), and hereinafter referred to by the name 'STO1.'

The new and distinct cultivar of cherry rootstock of the present invention was bred as a cross of *Prunus cerasus* with a wild *Prunus* sp. in Germany in 1989. It has been successfully asexually propagated by tissue culture since the first time in 2002. The purpose of the breeding program was to find better adapted cherry rootstocks. The new *Prunus* plant is better adapted on heat and aridity than other rootstocks with a slow vegetative growth. The breeder succeeded in creating a new cherry rootstock, which has a higher yield and influences the grafted variety positively in fertility.

SUMMARY OF THE INVENTION

Plants of the new *Prunus* have not been observed under all possible environmental conditions. The phenotype may vary slightly with variations in environment such as temperature and light intensity, without any variance in genotype.

The following traits have been repeatedly observed and are determined to be the unique characteristics of 'STO1.' These characteristics in combination distinguish 'STO1,' as a new and distinct cultivar of *Prunus:*

1. Upright plant habit;
2. Good adaptation to hot and dry clime conditions;
3. As a rootstock, with slow vegetative growth, it produces a dwarf tree;
4. As a rootstock, imparts uniformity and higher yield to the grafted variety as compared to, for example, Gisela 5, F12/1 and Mazzard; and
5. As a rootstock, grafted varieties have a 60% slower growth than a *Prunus avium* seedling; that is, the trees, for which 'STO1' is used as rootstock, grow more slowly and thus result in a dwarf tree that is smaller than, for example, a *Prunus avium* seedling.

As used herein, "higher yield" refers to the impact of the rootstock of the tree on both vegetative as well as generative growth. Thus, the rootstock can affect the generative growth and assist the grafted species to achieve greater yield. Therefore, with regard to 'STO1,' the yield per tree and crown volume is higher than that of a standard rootstock such as Gisela 5, F12/1 and Mazzard.

Further with 'STO1' as the rootstock, the grafted variety can achieve better fertility (i.e., greater generative growth). That is, use of 'STO1' as a rootstock results in greater generative growth than in the case of standard rootstock (Gisela 5, F12/1, Mazzard); the tree produces more flowers, more fruit, with a greater yield of the same or larger fruit size. In the end greater output is achieved.

The parents of 'STO1' are *Prunus avium* and *Prunus cerasus* wild species (both unnamed and not patented). The *Prunus cerasus* parent is known for slower growth and much finer wood (a greater number of branches and thinner branches) than 'STO1'. The *Prunus avium*-parent is known for stronger growth (i.e., faster growth) than 'STO1,' which results in much larger trees.

Plants of the new *Prunus*,'STO1,' also can be compared to plants of *Prunus* 'Weiroot 720' (U.S. Plant Pat. No. 22,867, issued Jul. 24, 2012). In side-by-side comparisons conducted in Kressbronn, Germany, plants of the new *Prunus* differed primarily from plants of 'Weiroot 720' in the following characteristics:

1. As a rootstock, plants of the new *Prunus* have a one-third stronger vegetative growth (i.e., faster growth) than plants with 'Weiroot 720' rootstocks;
2. Plants of the new *Prunus* develop stipules, whereas 'Weiroot 720' hasn't any stipules;
3. Plants of the new *Prunus* produce larger fruit. Average fruit diameter 'STO1': 1.9 cm, 'Weiroot 720': 1.2 cm. Average fruit weight 'STO1: 4 g, 'Weiroot 720': 1.6 g;
4. Due to its typical/characteristic growth, plants of the new *Prunus* impart higher yield to the scion plant than plants of 'Weiroot 720;' and
5. Fruits from plants of the new *Prunus* ripen about 10 days earlier than fruits from the 'Weiroot 720.'

'STO1' was first asexually propagated in 2002 in Freising, Germany, using tissue culture. Asexual reproduction of *Prunus* rootstock plant 'STO1' by tissue culture since 2002 has shown that the unique features of this new variety are stable and the plant reproduces true to type in succeeding generations of asexual reproduction.

BRIEF DESCRIPTION OF THE DRAWINGS

The accompanying photographs illustrate the overall appearance of the new *Prunus* plant. These photographs show the colors as true as it is reasonably possible to obtain in colored reproductions of this type. Colors in the photographs may differ slightly from the color values cited in the detailed botanical description which accurately describe the colors of the new *Prunus* plant.

DETAILED BOTANICAL DESCRIPTION

Figure 1:
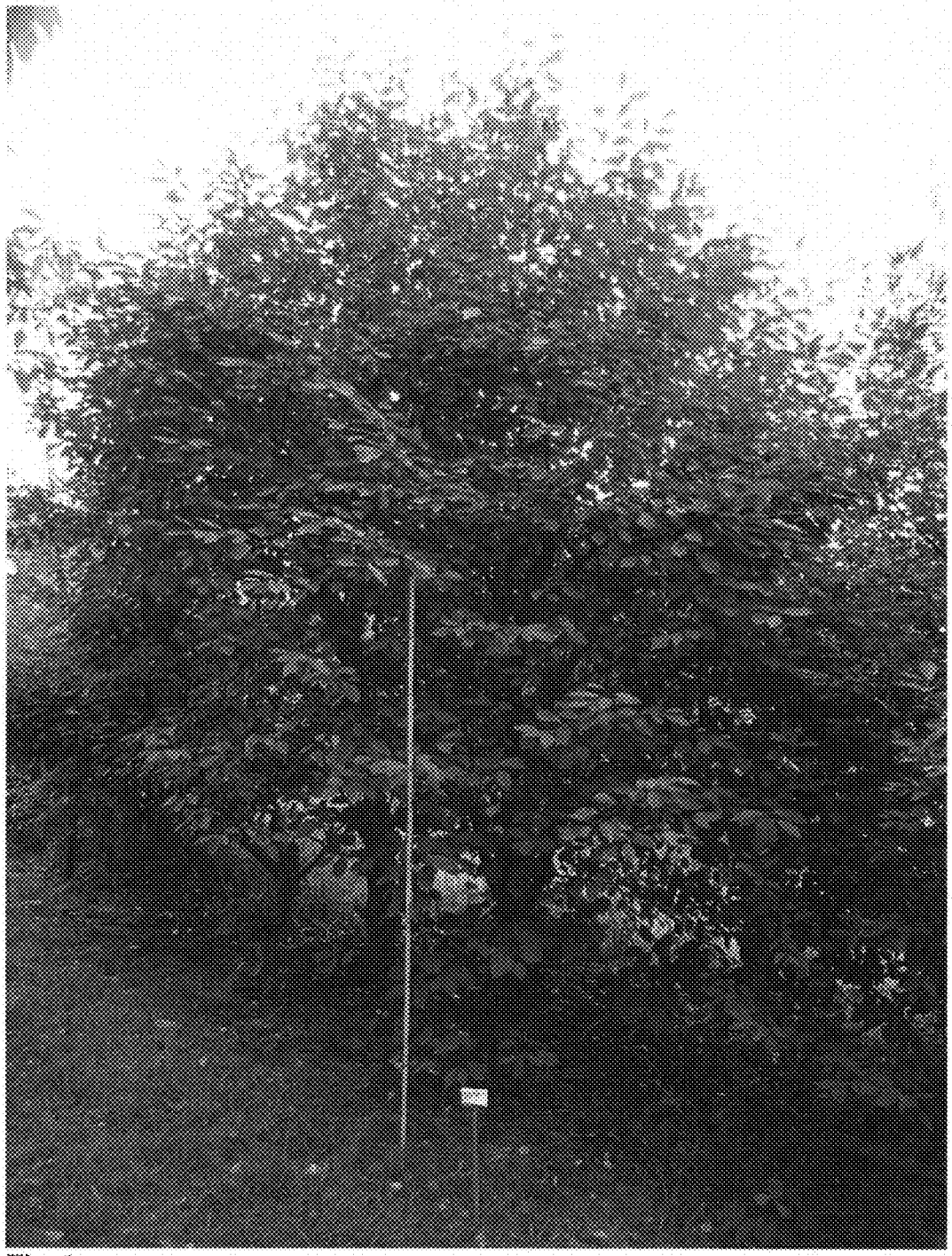
FIG. 1 provides a side perspective view of a typical tree of 'STO1' grown in an outdoor orchard.
Figure 2:
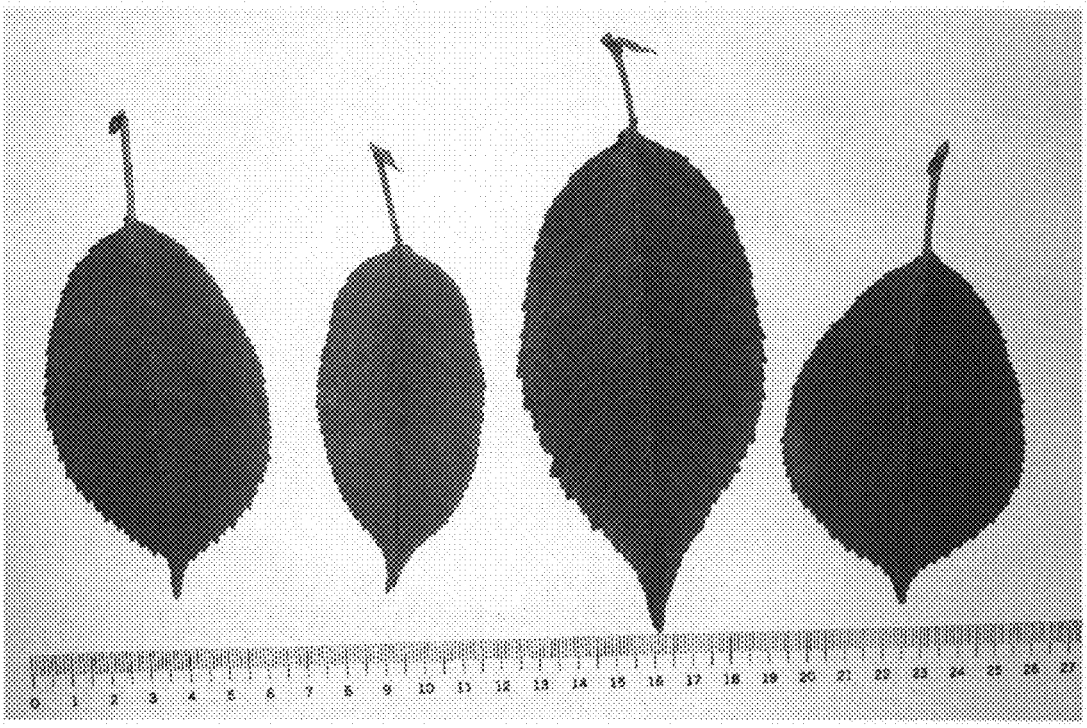
FIG. 2 provides a close-up view of leaves of 'STO1.'
Figure 3:
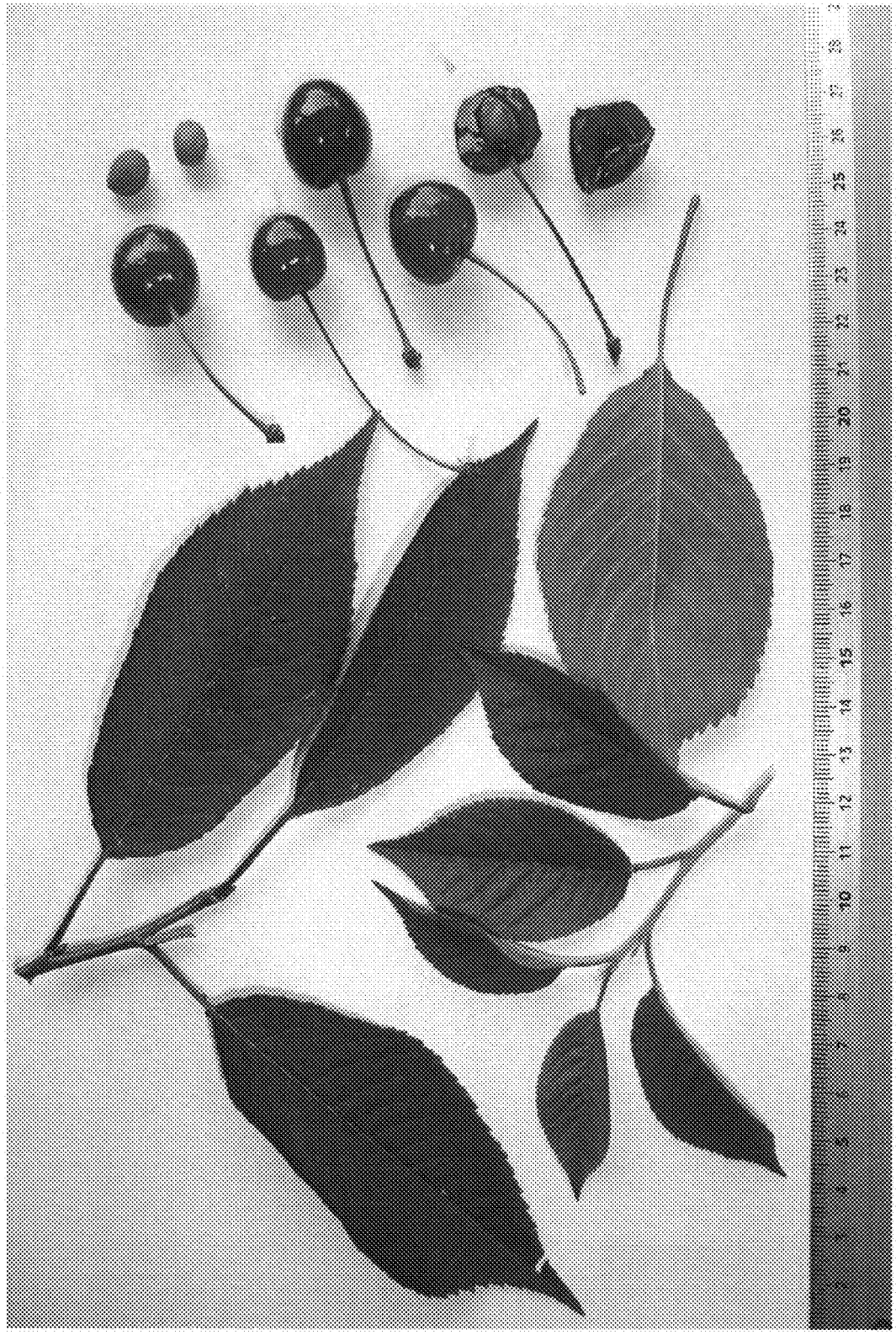
FIG. 3 provides a close-up view of fruits, branches and leaves of 'STO1'.

The aforementioned photographs, following observations and measurements describe plants grown during the summer in Kessbronn, Germany in an outdoor orchard and under conditions and practices generally used in commercial cherry production. Plants were 11 years old when the photographs and descriptions were taken. Measurements and numerical values represent averages for typical plants and plant parts. The actual measurements of any individual plant or plant parts, or any group of plants or plant parts, of the new *Prunus* plant may vary from the stated average. In the following description, color references are made to The Royal Horticultural Society (R.H.S.) Colour Chart, except where general terms of ordinary dictionary significance are used.

'STO1' has a generally erect plant habit and is medium strong in growth. After eleven growing seasons in Kressbronn, Germany, a height of about 4.8 meters, a width of about 3.5 meters and a trunk diameter of about 14 cm were observed for 'STO1 .' The growth reduction induced by 'STO1' allows a highly intensive cherry production with dwarf trees.

Botanical classification: *Prunus*×*gondouinii* (Poit. & Turpin) Rehder (*P. avium* (L.) L.×*P. cerasus* L.) 'STO1'.

Parentage: Breeding between *Prunus cerasus* and a *Prunus avium* species.

Propagation:

*Type.*—By asexual reproduction.

*Method.*—By tissue culture since 2002 in a controlled environment. The process is similar to the propagation of other cherry rootstocks.

Plant description:

*Plant and growth habit.*—Used a rootstock; upright plant habit; plants are typically grown as a single stem; moderate vigor.

*Stem description.*—Strength: Strong. Texture: Rough. Color: Grey brownish RHS 199B.

*Leaf description.*—Arrangement: Alternate; simple. Length: about 7.3 cm to about 12 cm. Width: about 4 cm to 7 cm. Shape: Ovate, moderately elongated to medium. Apex: Acute. Tip: Acuminate. Base: acute angle, flat curvature. Margin: Biserrate to serrulate. Texture, upper surface: Glabrous. Texture, lower surface: Pilose. Color: Fully developed leaves, upper surface: Close to RHS 137A; venation, close to RHS 141C. Fully developed leaves, lower surface: Close to RHS 137C; venation, close to RHS 161C.

*Petiole description.*—Length: about 2 cm to about 3 cm. Diameter: About 0.1 cm to about 0.21 cm. Color, upper surfaces and lower surfaces: Close to RHS173B.

*Presence of stipules.*—Present. Frequency: Not at every bud.

*Stipule description.*—Length: About 1.5 cm. Width: About 0.15 cm. Shape: Narrow, very elongated.

Flower description:

*Flower type/habit.*—2 to 4 single flowers arranged one compound panicles. Flowers occur in general on one year old branches.

*Fragrance.*—Weak, pleasant.

*Natural flowering season.*—In April, in south Germany, two days after 'Gisela 3.' Three days earlier than 'Weirood 720.'

*Lastingness of entire bloom period.*—About 16 days.

*Lastingness of an individual bloom.*—About 10 days.

*Inflorescence height.*—About 4.3 cm.

*Inflorescence diameter.*—About 4.5 cm.

*Bloom quantity.*—Fertile, a large quantity of flowers occur each year.

*Flower diameter.*—About 2.8 cm to about 3.1 cm.

*Flower depth.*—About 0.6 cm to about 1.5 cm. The pistil is very long, so the stigma overtops the anthers and the petals.

*Bud length.*—4-7 mm.

*Bud width* (*bud diameter*).—2-3 mm.

*Bud shape.*—Obtuse pointed, projecting.

*Bud colour.*—Dark brown — RHS-200B.

*Petals.*—Arrangement: Five petals in a single whorl, intermediate to slightly overlapping. Length: About 1.2 cm. Width: About 1.1 cm. Shape: Oblong, slightly elongated. Apex: Rounded, slightly elongated. Base: Truncate. Margin: Entire. Texture, upper and lower surfaces: Smooth, glabrous. Color: When fully opened, upper surface: Close to RHS 155B. When opening and fully opened, lower surface: Close to RHS 155D.

*Sepals.*—Arrangement: Five sepals in a single whorl. Length: About 0.5 cm. Width: About 0.28 cm. Shape: Ovate, moderately elongated. Apex: Rounded. Base: Truncate. Margin: Entire. Texture, upper and lower surfaces: Smooth, glabrous. Color, upper surfaces: Close to RHS 142A. Color, lower surfaces: between RHS 134A and RHS 185A.

*Pedicels.*—Length: About 2.15 cm. Diameter: About 0.1 cm. Angle: About semi-erect to semi-prostrate from the inflorescence stalk. Texture: Smooth, glabrous. Color: Close to RHS 142A.

*Peduncle.*—Length: About 0.2 cm. Diameter: About 0.1 cm. Surface: Smooth. Color: Close to RHS 149A.

*Reproductive organs.*—Stamens: Quantity per flower: Numerous. Filament length: About 3 mm to about 10 mm. Filament color: Close to RHS 155B. Anther length: About 0.5 mm to about 1.3 mm. Anther color: Close to RHS 6A. Pollen color: Close to RHS 6D. Pistils: Quantity per flower: One. Pistil length: About 9 mm to about 16 mm. Style length: About 8 mm to about 11 mm. Style color: Close to RHS 154B. Stigma shape: Round. Stigma color: Close to RHS 154A.

*Fruit description.*—Maturity when described. Date picking: July in south Germany, varies with climatic conditions. About ten days earlier than 'Weiroot 720', (U.S. Plant Pat. No. 22,867). Size: small to medium size; about 1.6 cm to about 2.1 cm diameter. Average weight: About 4 g, varies slightly with fertility of the soil, amount of thinning and climatic conditions. Form: Globose, Slightly flat at the apex. Stem cavity: Slightly obcordate to flat. Color: RHS 53A.

*Peduncle description.*—Length: about 3.2 cm to about 5.2 cm. Average diameter about 0.09 cm. Color: RHS 179A.

*Stone description.*—Average length: About 1 cm. Average width: About 0.8 cm. Average thickness: About 0.65 cm. Form: Nearly ovoid. Base: Flat. Apex: Obtuse. Color: RHS 164B when dry.

*Fruit use.*—Not to be used as a dessert fruit.

Pollination requirements: "STO1' is not self-fertile and requires a pollinator.

Temperature tolerance: Plants of the new *Prunus* have been observed to tolerate temperatures from about −20° C. to about 40° C. Notably, under hot and dry climatic conditions, 'STO1' trees do not exhibit chlorosis. These trees are very robust in the presence of substantial variations in temperature (very low temperatures in winter (−20° C.) and very hot temperatures in summer (+40° C.)) and such temperature fluctuations have no negative effect on the trees.

Drought tolerance: Due to a deep root system, the new variety, 'STO1,' is tolerant to drought conditions.

What is claimed is:

1. A new and distinct cultivar of *Prunus*×*gondouinii* (Poit. & Turpin) Rehder (*P. avium* (L.) L.×*P. cerasus* L.) plant named 'STO1', substantially as illustrated and described herein.

* * * * *

UNITED STATES PATENT AND TRADEMARK OFFICE

CERTIFICATE OF CORRECTION

PATENT NO. : PP25,891 P3
APPLICATION NO. : 13/987744
DATED : September 15, 2015
INVENTOR(S) : Stoppel It is certified that error appears in the above-identified patent and that said Letters Patent is hereby corrected as shown below:

On Title Page:

(50) Latin Name: Please correct

"*Prunus*x*gondouinii* (Poit. & Turpin) Rehder (*P. avium* (L.) L.xP. *cerasus* L.)"

to read

-- *Prunus* x *gondouinii* (Poit. & Turpin) Rehder (*P. avium (L.) L.* x *P. cerasus L.)* --

In the Specification:

Column 1, Lines 3-4: Please correct

"*Prunus*x*gondouinii* (Poit. & Turpin) Rehder (*P. avium* (L.) L.xP. *cerasus* L.)."

to read

-- *Prunus* x *gondouinii* (Poit. & Turpin) Rehder (*P. avium (L.) L.* x *P. cerasus L.).* --

Column 1, Lines 5-6: Please correct

"*Prunus*x*gondouinii* (Poit. & Turpin) Rehder (*P. avium* (L.) L.xP. *cerasus* L.)"

to read

-- *Prunus* x *gondouinii* (Poit. & Turpin) Rehder (*P. avium (L.) L.* x *P. cerasus L.)* --

Column 1, Lines 14-15: Please correct

"*Prunus*x*gondouinii* (Poit. & Turpin) Rehder (*P. avium* (L.) L.xP. *cerasus* L.),"

to read

-- *Prunus* x *gondouinii* (Poit. & Turpin) Rehder (*P. avium (L.) L.* x *P. cerasus L.)*, --

Column 4, Lines 8-9: Please correct

"*Prunus*x*gondouinii* (Poit. & Turpin) Rehder (*P. avium* (L.) L.xP. *cerasus* L.)"

to read

-- *Prunus* x *gondouinii* (Poit. & Turpin) Rehder (*P. avium (L.) L.* x *P. cerasus L.)* --

Signed and Sealed this
Seventeenth Day of May, 2016

Michelle K. Lee

Michelle K. Lee
*Director of the United States Patent and Trademark Office*

In the Claims:

Column 6, Lines 29-30: Please correct

"*Prunus*x*gondouinii* (Poit. & Turpin) Rehder (*P. avium* (L.) L.xP. *cerasus* L.)"

to read

-- *Prunus* x *gondouinii* (Poit. & Turpin) Rehder (*P.* avium *(L.) L.* x *P. cerasus L.)* --